United States Patent
Carolus et al.

(10) Patent No.: US 10,210,310 B2
(45) Date of Patent: Feb. 19, 2019

(54) PICTURE ARCHIVING SYSTEM WITH TEXT-IMAGE LINKING BASED ON TEXT RECOGNITION

(71) Applicant: KONINKLIJKE PHILIPS N.V., Eindhoven (NL)

(72) Inventors: Heike Ruppertshofen Carolus, Hamburg (DE); Thusitha Dananjaya De Silva Mabotuwana, Bothell, WA (US); Yuechen Qian, Lexington, MA (US); Juergen Weese, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/522,324

(22) PCT Filed: Nov. 2, 2015

(86) PCT No.: PCT/IB2015/058464
§ 371 (c)(1),
(2) Date: Apr. 27, 2017

(87) PCT Pub. No.: WO2016/071825
PCT Pub. Date: May 12, 2016

(65) Prior Publication Data
US 2017/0337328 A1    Nov. 23, 2017

Related U.S. Application Data

(60) Provisional application No. 62/074,108, filed on Nov. 3, 2014.

(51) Int. Cl.
*G06K 9/00* (2006.01)
*G06F 19/00* (2018.01)
*A61B 5/00* (2006.01)

(52) U.S. Cl.
CPC ............ *G06F 19/321* (2013.01); *A61B 5/004* (2013.01); *G06F 19/00* (2013.01)

(58) Field of Classification Search
CPC .............................. A61B 5/004; G06F 19/321
(Continued)

(56) References Cited

U.S. PATENT DOCUMENTS 8,254,649 B2 * 8/2012 Matsue ................. G06F 19/321
                                                          382/128
8,423,571 B2    4/2013 Yoshiyuki
(Continued)

OTHER PUBLICATIONS

Mabotuwana, T., et al., "Using image references in radiology reports to support enhanced report-to-image navigation", AMIA Annu Symp Proc., 2013:908-16.
(Continued)

*Primary Examiner* — Charlotte M Baker

(57) ABSTRACT

A method includes visually displaying an electronically formatted medical report, wherein the electronically formatted medical report references a set of electronically formatted images, acquiring the set of electronically formatted images, and linking the electronically formatted medical report and the set of electronically formatted images. A computing apparatus (102), includes a memory (108) with at least one computer readable instruction (106) and a processor (104) that executes the at least one computer readable instruction. The processor, in response to executing the at least one computer readable instruction, visually displays an electronically formatted medical report, wherein the electronically formatted medical report references a set of electronically formatted images, acquires the set of electronically formatted images, and links the electronically formatted medical report and the set of electronically formatted images.

15 Claims, 7 Drawing Sheets

(58) Field of Classification Search
USPC ...... 382/128, 131; 704/9, 235; 707/E17.008; 715/205, 234; 345/636
See application file for complete search history.

(56) References Cited

U.S. PATENT DOCUMENTS

| | | | |
|---|---|---|---|
| 9,053,563 B2 * | 6/2015 | Embrey | G06T 17/00 |
| 2003/0154071 A1 * | 8/2003 | Shreve | G06F 17/2845 |
| | | | 704/9 |
| 2008/0253631 A1 | 10/2008 | Oosawa | |
| 2012/0176408 A1 | 7/2012 | Yoshiyuki | |
| 2013/0006087 A1 | 1/2013 | Kondo et al. | |
| 2014/0006926 A1 | 1/2014 | Yeluri et al. | |
| 2014/0081623 A1 | 3/2014 | Bretschneider et al. | |
| 2014/0142939 A1 * | 5/2014 | Aradi | G10L 15/265 |
| | | | 704/235 |
| 2014/0195266 A1 | 7/2014 | Mistry et al. | |
| 2014/0316770 A1 | 10/2014 | Sevenster et al. | |

OTHER PUBLICATIONS

Mabotuwana, T. et al., "Determining scanned body part from DICOM study description for relevant prior study matching", Stud Health Technol Inform., 2013;192:67-71.

Sevenster, M. et al., "Automatically correlating clinical findings and body locations in radiology reports using MedLEE," J. Digit Imaging, No. 25, pp. 240-249, 2012.

Vik, T. et al., "A new method for robust organ positioning in CT images," in IEEE International Symposium on Biomedical Imaging (ISBI), 2012.

Brandt, R. et al., "Quo Vadis, Atlas based segmentation", in the Handbook of Medicl Image Analysis: Segmentation and Registration Models, Kluwer, 2005.

El-Kwae, E.A. et al., "Content-Based Retrieval in Picture Archiving and Communication Systems". Journal of Digital Imaging, vol. 13, No. 2 (May), 2000: pp. 70-81.

* cited by examiner

PICTURE ARCHIVING SYSTEM WITH TEXT-IMAGE LINKING BASED ON TEXT RECOGNITION

CROSS-REFERENCE TO PRIOR APPLICATIONS

This application is the U.S. National Phase application 35 U.S.C. § 371 of International Application No. PCT/IB2015/058464, filed on Nov. 2, 2015, which claims the benefit of U.S. Provisional Application No. 62/074,108, filed on Nov. 3, 2014. This application is hereby incorporated by reference herein.

FIELD OF THE INVENTION

The following generally relates to linking a medical report and an image(s) referenced therein.

BACKGROUND OF THE INVENTION

Reporting can be a time-consuming part in the daily routine of a radiology department. The typical radiology reporting workflow involves the radiologist looking through a plurality of images of an imaging study and writing or dictating a narrative report describing the observed findings. Along with the finding description, oftentimes the radiologists would also include references to specific image slices (e.g., "Neurofibroma in the superior right extraconal space (series 5, image 104) measuring approximately 17 mm"). These specific references often correspond to key images.

The report is created and stored in the Radiology Information System (RIS), while the images are stored in the Picture Archiving System (PACS). In the PACS user interface, tools are available to make basic measurements, e.g., length or mean Hounsfield Unit HU value in a region of interest (ROI), or annotations, e.g., arrows, to mark interesting regions in the image. Usually there is an integrated solution such that images in the PACS are more or less linked to the patient health record. However, there is no association between the images and/or annotations on the images and the findings in the report.

SUMMARY OF THE INVENTION

Aspects described herein address the above-referenced problems and others.

In one aspect, a method includes visually displaying an electronically formatted medical report, wherein the electronically formatted medical report references a set of electronically formatted images, acquiring the set of electronically formatted images, and linking the electronically formatted medical report and the set of electronically formatted images.

In another aspect, a computing apparatus (102), includes a memory (108) with at least one computer readable instruction (106) and a processor (104) that executes the at least one computer readable instruction. The processor, in response to executing the at least one computer readable instruction, visually displays an electronically formatted medical report, wherein the electronically formatted medical report references a set of electronically formatted images, acquires the set of electronically formatted images, and links the electronically formatted medical report and the set of electronically formatted images.

In another aspect, a computer readable storage medium encoded with computer readable instructions, which, when executed by a processer, causes the processor to: visually display an electronically formatted medical report, wherein the electronically formatted medical report references a set of electronically formatted images, acquire the set of electronically formatted images, and link the electronically formatted medical report and the set of electronically formatted images.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
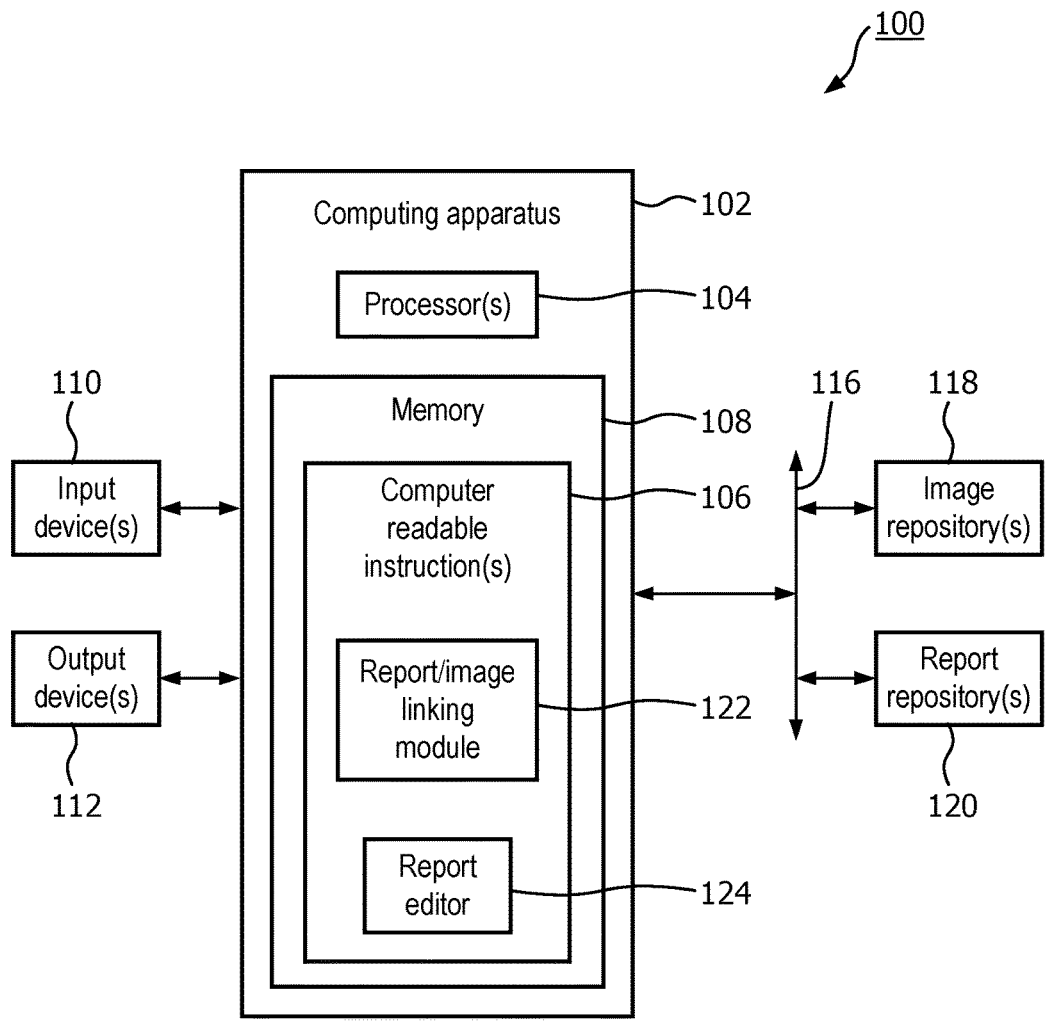
FIG. 1 schematically illustrates an example computing system with a report/image linking module.

FIG. 1 schematically illustrates a system 100. The system 100 includes a computing apparatus 102. The computing apparatus 102 includes a processor(s) 104, which executes a computer readable instruction(s) 106 stored in computer readable storage medium ("memory") 108, which excludes transitory medium and include physical memory and/or other non-transitory storage medium. The processor 104 can also execute one or more computer readable instructions carried by a carrier wave, a signal or other transitory medium. The computing apparatus 102 includes an input device(s) 110 such as a keyboard, a mouse, a touch screen, etc., and an output device(s) 112 such as a display monitor, etc.

The computing apparatus 102 is in communication with, through a network 116, an image repository(s) 118 that stores electronically formatted images. An example of an image repository(s) 118 is a picture archiving and communication system (PACS), a database, etc. The computing apparatus 102 is also in communication with, through the network 116, a report repository(s) 120 that stores electronically formatted reports. An example of the report repository(s) 120 is radiology information system (RIS), a database, etc. Other systems that may store images and/or reports include a hospital information system (HIS), an electronic medical record (EMR), etc. The images can be CT, MR, PET, SPECT, X-ray, etc. images.

The computing apparatus 102 can be a clinical support system, a computer, etc. located at a physician's office, a health care facility, an imaging center, etc. The computer readable instruction 106 includes a report/image linking module 122, which, when executed by the processor 104 causes the processor 104 to process a report and a set of corresponding images. As described in greater detail below, the processor 104, in response to executing instructions of the report/image linking module 122, links the report and the set of corresponding images. With the linking, a radiologist creating/viewing the report need not to have to search for, find, and retrieve the corresponding set of images, and a radiologist viewing the set of images need not to have to search for, find, and retrieve the corresponding report.

Figure 2:
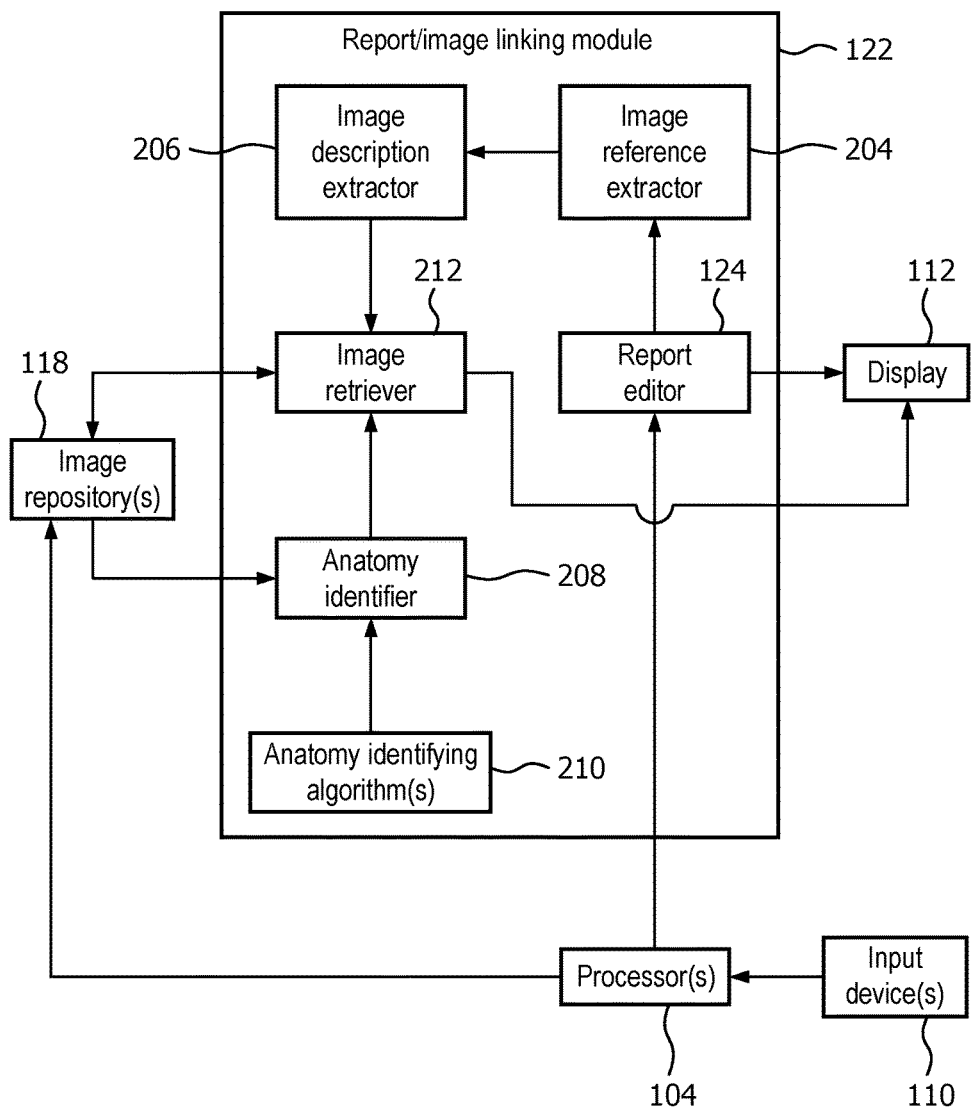
FIG. 2 schematically illustrates an example of the report/image linking module.

FIG. 2 schematically illustrates an example of the report/image linking module 122. The report/image linking module 122 includes a report editor 202, which allows for creating a new report and/or editing an existing report. In one example, the report editor 202 visually presents, via a display output device 112, a graphical user interface with a report creation/editing window.

The report/image linking module 122 further includes an image reference extractor 204. In one instance, the image reference extractor 204 employs a natural language processing (NLP) algorithm to extract an image reference(s) from a current report. In one example, the image reference extractor 204 uses the NLP algorithm to determine sections, paragraphs, sentences, etc. from the report.

The image reference extractor 204 processes the sentences in the "Finding" section of the report and extracts, for instance, using regular expressions and image references from one or more of the sentences. With one report, this may include extracting: "series 11" and "image number 79" from a sentence "The left hepatic reference lesion (series number 11, image number 79) measures approximately 6.4×5.4 cm."

An example of a suitable algorithm is described in Mabotuwana T, Qian Y, Sevenster M., "Using image references in radiology reports to support enhanced report-to-image navigation." AMIA Annu Symp Proc., 2013:908-16. Other algorithms are also contemplated herein.

In a variation, the image reference extractor 204 also extracts, at a sentence level, date information that a sentence may contain. For instance, for the sentence "On the 16 Oct. 2011 scan, nodule measures 3 cm (series 5, image 26)", the image reference extractor 204 extracts: "series 5", "image 26", "16 Oct. 2011."

The report/image linking module 122 further includes an image description extractor 206. The image description extractor 206 processes the sections, paragraphs, sentences, etc. of the reports. In one instance, this includes utilizing a maximum entropy classifier to assign an end-of-sentence marker ('.', ':', '!', '?', 'n') in the text one of four labels: Not end of sentence (e.g., period in 'Dr. Doe'); End of sentence, and sentence is a section header (e.g., Colon in Findings: section); End of sentence, and sentence is the last sentence in a paragraph, and End of sentence and none of the above classes.

The image description extractor 206, for each sentence where an image reference was extracted, uses standard NLP techniques to identify the main noun phrase associated with the image reference. For example, from the phrase "The left hepatic reference lesion (series number 11, image number 79) measures approximately 6.4×5.4 cm," the image description extractor 206 extracts "left hepatic reference lesion" as the key noun phrase associated with the image reference.

In another embodiment, where an explicit image reference is not mentioned in the report text, the entire section-paragraph-sentence structure can be reconstructed. In a post-processing step, recognized section headers (e.g., Findings) and paragraph headers (e.g., PANCREASE, LIVER etc.) are normalized with respect to a list of known headers.

Once this is done, the image description extractor 206 identifies the noun phrases associated with each paragraph header. Priority will be given to noun phrases that have a matching measurement.

Identifying noun phrase based on matching measurement alone is also possible instead of measurement and body part/organ. When no measurements are present, the extracted information (i.e., paragraph headers and noun phrases) is combined with the identified organ to determine the description associated with key images. When the image is annotated with a finding description (e.g., "pancreatic mass"), this information is used as the description associated with the key image.

The report/image linking module 122 further includes an anatomy identifier 208. The anatomy identifier 208 identifies anatomy in images of studies where a measurement is made. In one instance, this information is identified from the DICOM "Study Description Field," the "Protocol Name Field," the "Series Description Field" and/or other field that contain anatomy related information. For instance, where one of these fields includes "pancreatic mass," the anatomy identifier 208 identifies the "pancreas."

Where two or more of these DICOM fields and/or other DICOM fields include anatomy related information, a rule-based and/or other approach can be used to identify the anatomy in the study of interest where a measurement is made. An example of a suitable algorithm is described in Mabotuwana T, Qian Y, "Determining scanned body part from DICOM study description for relevant prior study matching." Stud Health Technol Inform., 2013;192:67-71.

Figure 3:
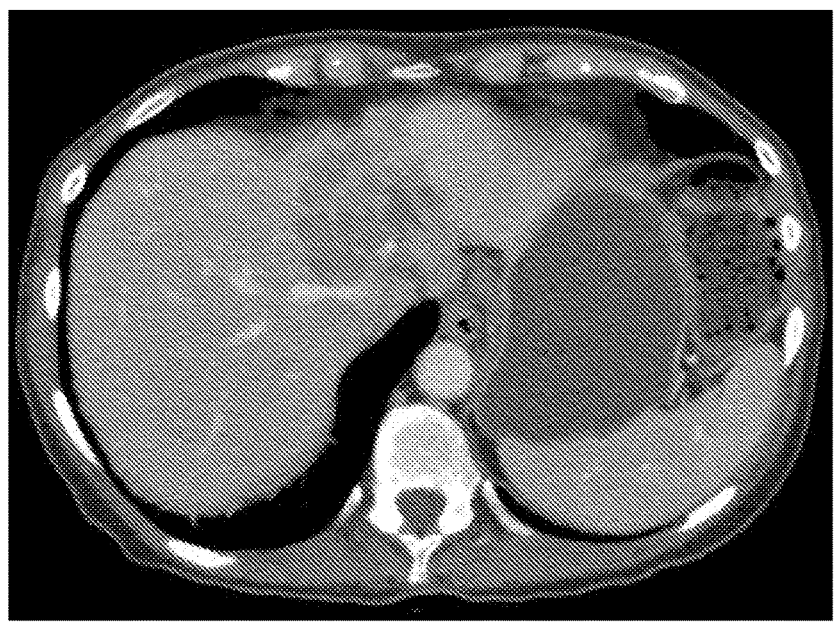
FIG. 3 illustrates an example image without a measurement or annotation thereon.
Figure 4:
FIG. 4 illustrates an example image with a measurement but no annotation thereon.
Figure 5:
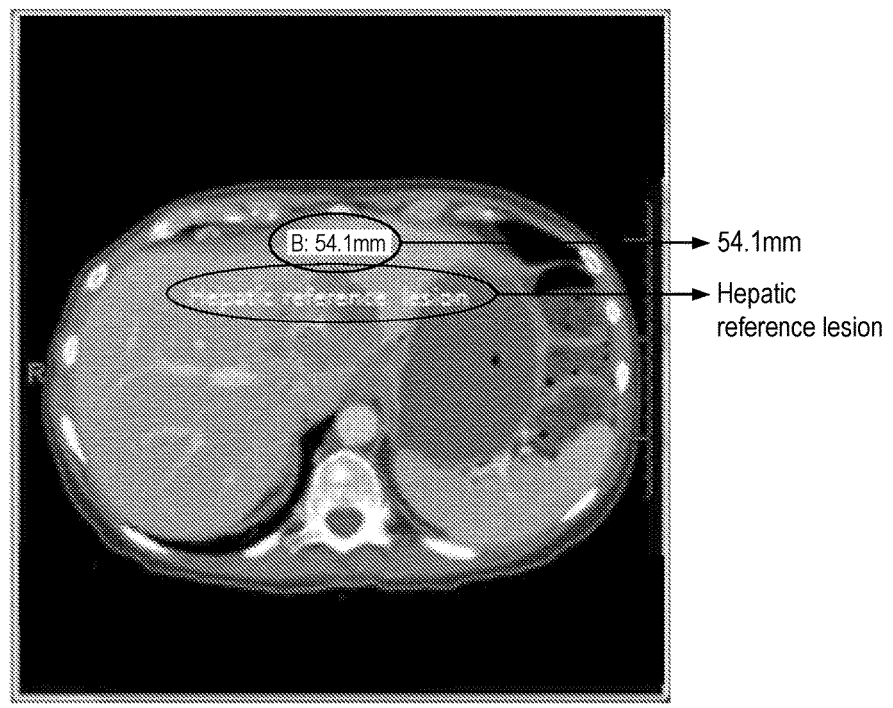
FIG. 5 illustrates an example image with a measurement and an annotation thereon.

In a variation, the anatomy identifier 208 identifies the anatomy from textual, numerical, graphical, etc. image overlay. The illustrated anatomy identifier 208 utilizes an algorithm from anatomy identifying algorithm(s) 210. FIGS. 3, 4, and 5 illustrate non-limiting algorithms. In FIG. 3, the organ "liver" is extracted from the DICOM field. In FIG. 4, a measurement value "54.1 mm" is additionally extracted from the image. In FIG. 5, the text "Hepatic reference lesion" is additionally extracted from the image, indicating the "liver."

Returning to FIG. 2, the report/image linking module 122 further includes an image retriever 212. The image retriever 212 retrieves the identified image(s) from the image repository(s) 118. For instance for the parsed input "series 5", "image 26", "16 Oct. 2011", the image retriever 212 communicates with the image repository(s) 118 to determine the internal DICOM information required to fetch the related image from the image repository(s) 118.

The retrieved image(s) is then associated with the description determined by the image description extractor 206. The image retriever 212 visually presents the retrieved image(s) in an image window in the graphical user interface visually presented through the display 112. In one instance, the image window is presented alongside the report creation/editing window. In another instance, the image window is presented alternative to the report creation/editing window.

Figure 6:
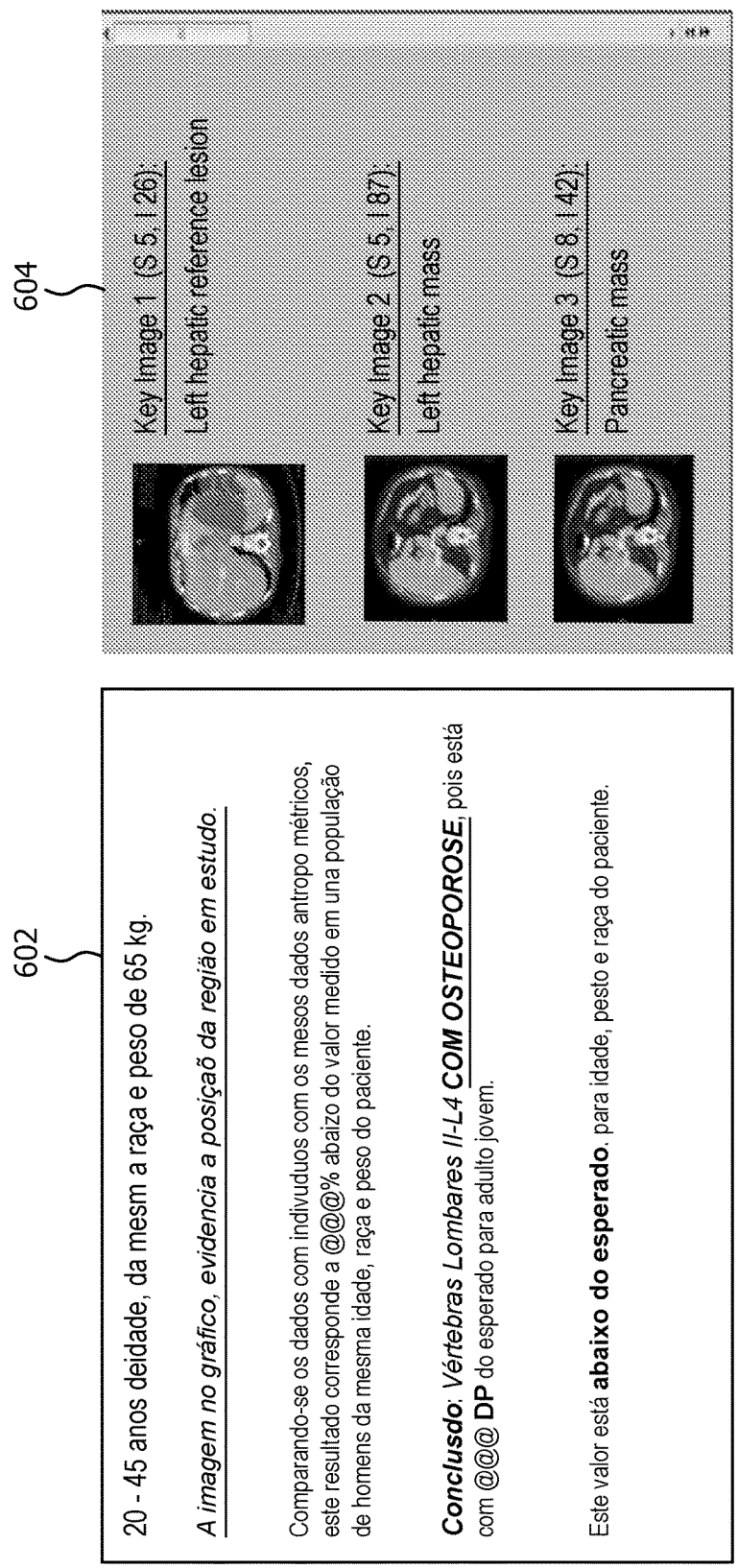
FIG. 6 illustrates an example report creating/editing window and an image window.

An example of a report creation/editing window 602 and a concurrently displayed image(s) window 604 are shown in FIG. 6. In this example, the image(s) window 604 includes a plurality of images with corresponding information. The image(s) window 604 allows the user to move, copy, etc. the information from the image(s) window 604 into the report in the report creation/editing window 602. The user can also update/edit the finding description in the image window 604 or the reporting environment in the report creation/editing window 602 directly.

Figure 7:
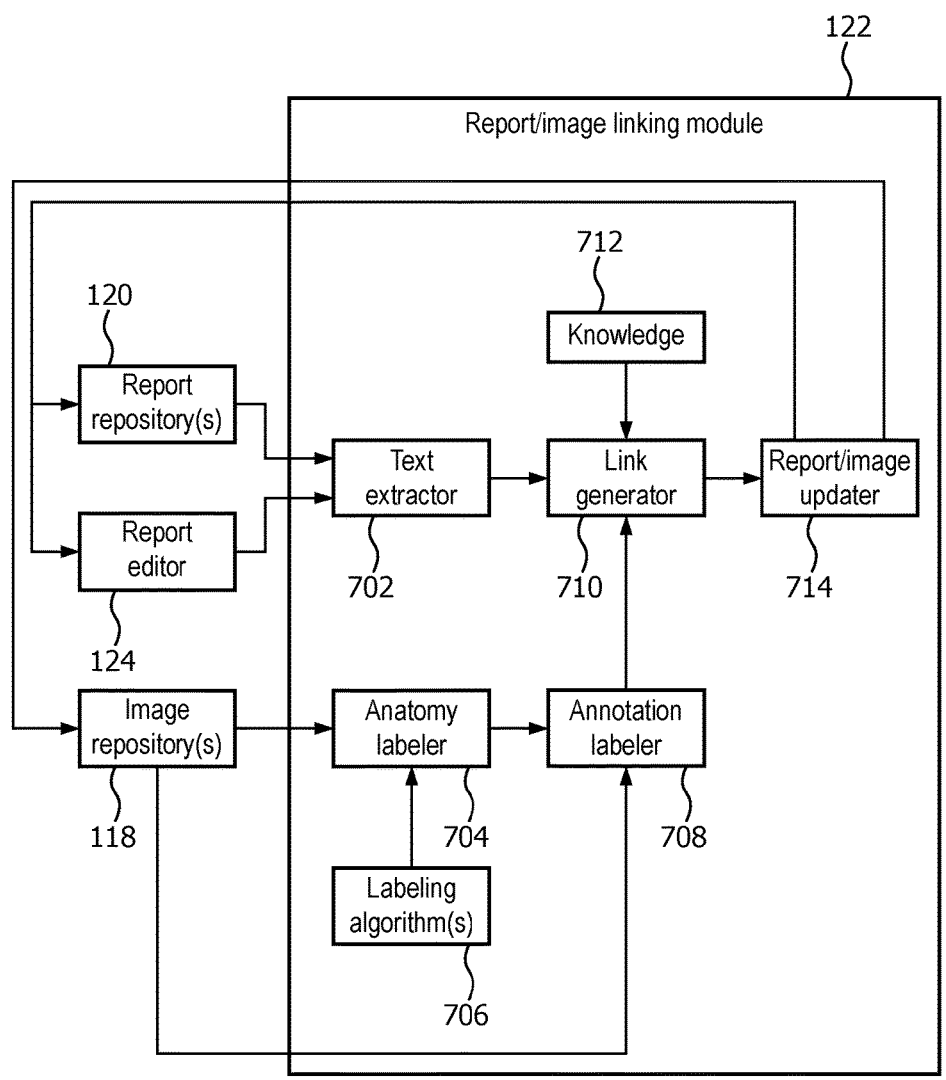
FIG. 7 schematically illustrates another example of the report/image linking module.

Turning to FIG. 7, another example of the report/image linking module 122 is schematically illustrated. In general, in this embodiment, the report/image linking module 122 generates a link between findings in an image, which are marked by annotations, and the corresponding keyword in the report. This includes automatically linking keywords in a report with annotations in the image. These annotations can be measurements, arrows, or markings from any other available tool.

In this example, the report/image linking module 122 includes a text extractor 702. The text extractor 702 extracts keywords, e.g., the diagnosis, abnormalities, measurements, locations and/or other information from a report while or after the report is written or dictated. A previously generated report can be obtained from the report repository(s) 120. A report currently being created can be obtained from the report editor 124.

The text extractor 702, in one instance, extracts keywords using a NLP algorithm. An example of a suitable algorithm is described in M. Sevenster et al., "Automatically Correlating Clinical Findings and Body Locations in Radiology Reports Using MedLEE," J Digit Imaging, no. 25, pp. 240-249, 2012. Other algorithms are also contemplated therein. The text extractor 702 outputs a signal including a list of findings with their corresponding anatomical location.

The report/image linking module 122 further includes an anatomy labeler 704. The anatomy labeler 704 labels anatomy in images. For example, the anatomy labeler 704 processes an image to identify the tissue (e.g., heart) therein and the location of the tissue. In one instance, the level of detail of the anatomy detection are such that organs like a heart chamber, a liver lobe, a cortical area in the brain, etc. as usually stated in reports can be coarsely identified.

For this, a hierarchical allocation can be employed to first detect a body part (e.g., thorax), then an organ (e.g., heart), and then a precise location (e.g., left atrium) if the confidence of the detection is high enough. In the illustrated embodiment, the anatomy labeler 704 employs an anatomy labeling algorithm form the labeling algorithm(s) 706. Such algorithms include an atlas based, a statistical based, and/or other anatomy labeling algorithm.

If an atlas algorithm is used, this information could be directly encoded also taking the hierarchical structure into account. In a variation, a model that provides knowledge about anatomy in a navigable and parseable manner can be integrated therewith. With a statistical algorithm, the detection of anatomy need not be exact, but rather a likely decision. For example, a certain location can be assigned, e.g., to the heart with a probability of 0.4 and to the liver with a probability of 0.6.

The images can be obtained from the image repository(s) 118 and/or other source. Suitable algorithms include Vik e al., "A new method for robust organ positioning in CT images," in IEEE International Symposium on Biomedical Imaging (ISBI), 2012, Rohlfing et al., "Quo Vadis, Atlas-Based Segmentation," in The Handbook of Medical Image Analysis: Segmentation and Registration Models, Kluwer, 2005, and/or one or more other algorithms.

The report/image linking module 122 further includes an annotation labeler 708. The annotation labeler 708 labels annotation on the images. The illustrated annotation labeler 708 maps the anatomical labels assigned to the image by the anatomy labeler 704 to the annotations on the image. For instance, an annotation on the image corresponding to the location of anatomy the label "heart" is assigned the label "heart." In this way, each annotation is assigned to particular anatomy based on the anatomy labeled image.

The annotations (e.g., length or volume measurement, arrow, mean HU value measurement, etc.) can be made with known or other tools, which makes markings on the image. The annotations may also include "invisible bookmarks", which are marks made on the image that are not shown, e.g., to avoid cluttering and thereby distraction of the reporting physician. The resulting set of labeled annotations can be stored internally as a list and/or otherwise.

By way of non-limiting example, for an invisible bookmark, when a clinician encounters something of interest, the clinician can click on the position in the image. A marker, e.g., a little cross, can be temporarily visually displayed at the region of the click and then made transparent or invisible. These bookmarks are stored and also used for linkage with the report. An invisible bookmark can be visually displayed again on request and/or otherwise, e.g., for editing.

The report/image linking module 122 further includes a link generator 710. The link generator 710 creates a link between the extracted text in a report and the labeled annotations. For example, the link generator 710 processes the list of findings and the list of annotations and correlates their positions. For this, the link generator 710 utilizes knowledge 712 about the anatomy and the ontological relationship as it must be able to deal with precise anatomical locations like aortic valve as well as coarser descriptions like upper abdomen.

The link generator 710 identifies the most likely combinations of findings and annotations. In one instance, the link generator 710 achieves a predetermined sensitivity (e.g., 100%, 90%, 75%), etc.) such that only valid links are created. If in doubt, a link can either be left out or the user could be prompted to confirm. The link generator 710, in response to matching a finding in the report and an annotation in the image, creates a link such as a hyperlink for both the report and the image.

In one instance, the link generator 710 generates a link automatically using anatomical knowledge. That is, for every annotation the anatomical location needs to be known such that it can be automatically linked to findings and their location mentioned in the report. For example, the link generator 710 can generate a link to the finding "hepatocellular carcinoma in the right liver lobe" to a measurement which was automatically determined to be in the right liver lobe.

The report/image linking module 122 further includes a report/image updater 714. The report/image updater 714 adds the report hyperlink to the report. The report hyperlink, in response to being invoked, retrieves the linked image, which can be displayed and/or otherwise used. The report/image updater 714 further adds the image hyperlink to the image. The image hyperlink, in response to being invoked, retrieves the linked report, which can be displayed and/or otherwise used.

The hyperlink can be invoked via an input through an input device(s) 110, e.g., by clicking using a mouse. This means that by clicking onto the hyperlink in the report, the report repository(s) 120 shows the image at the slice corresponding to the annotation, and by clicking onto the annotation the corresponding report is shown at the position of the finding. This can be especially helpful if older reports or acquisitions are taken into account in a current reporting session.

In a variation, the link generator 710 could learn about likely and unlikely combinations of findings and location of annotations, e.g., an artificial heart valve will always be in the heart, while a fracture will never correspond to an annotation on soft tissue. It could also know about the combination of certain diagnoses and annotation types, e.g., tumors or stents to diameter measurements, bleedings to HU value measurement, fractures or aneurysms to arrows.

In another variation, the link generator 710 can link a finding over several studies such that by clicking on a tumor hyperlink in the current report, the tumor is not only shown in the current study but also in the previous one. The linking may be between annotations to findings for a PACS-RIS and/or other tools like a timeline which shows the examinations and findings of a patient in a temporally structured manner.

The link can be helpful in various scenarios. For example, in some situations a report is first drafted by a resident and then proof-read by an attending physician. By linking the keywords in the report to the location in the image, which led to this diagnosis, the attending physician could comprehend more easily in unclear cases how the resident arrived at that diagnosis. This could lead to a faster and easier review of the report.

In another example, when prior reports are consulted in follow-up scenarios, hyperlinks could help in understanding the prior diagnosis faster and also allow for a faster comparison of suspicious regions. In another example, the hyperlinks can be used for teaching. Here as well, hyperlinks between diagnostic findings and the corresponding image can help to review a case faster.

Figure 8:
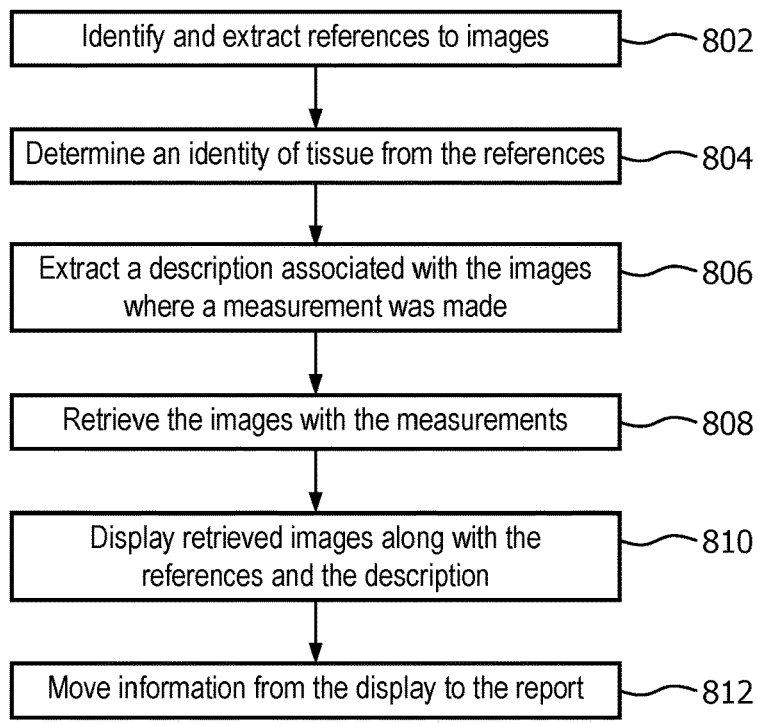
FIG. 8 illustrates an example method for linking a report and an image.

FIG. 8 illustrates an example method in accordance with the disclosure herein.

It is to be appreciated that the ordering of the acts in the methods described herein is not limiting. As such, other orderings are contemplated herein. In addition, one or more acts may be omitted and/or one or more additional acts may be included.

At 802, references to images in a current medical report are identified in and extracted from the medical report.

At 804, an identity of tissue is determined from each extracted reference.

At 806, a description associated with the images where a measurement was made is extracted from each of the extracted reference.

At 808, the images in the references where there is a measurement are retrieved.

At 810, the retrieved images are associated with the identity of tissue from the extracted references.

At 810, the retrieved images are displayed in an image window along with the references and the description.

At 812, in response to a user input via the input device(s) 110, the processor 104 moves information selected in the image window to the report in the report creating/editing window.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

Figure 9:
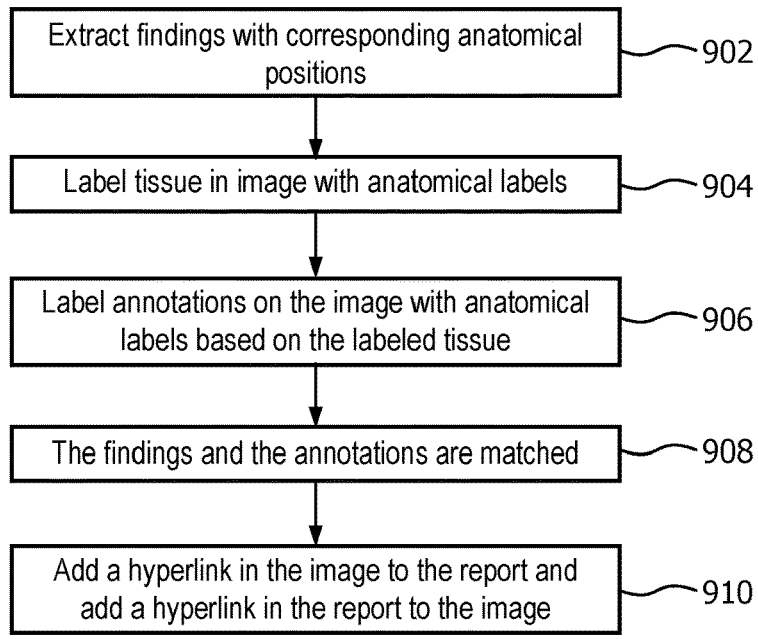
FIG. 9 illustrates another example method for linking a report and an image.

FIG. 9 illustrates an example method in accordance with the disclosure herein.

At 902, findings and corresponding anatomical positions are extracted from a medical report.

At 904, tissue in an image is labeled with anatomical labels, as described herein and/or otherwise.

At 906, annotations on the image are labeled with anatomical labels based on the labeling of the tissue in the image.

At 908, the findings and the annotations are matched.

At 910, a hyperlink to the image is inserted into the report at the location of the finding, and a hyperlink to the report is added to the image at the location of the annotation.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
   visually displaying an electronically formatted medical report, wherein the electronically formatted medical report references a set of electronically formatted images;
   extracting the references to the set of electronically formatted images from the electronically formatted medical report;
   linking the electronically formatted medical report and the set of electronically formatted images by:
      determining, from the extracted references, an identity of tissue in each image of the set of electronically formatted images where a measurement was made;
      extracting, from the extracted references, a description associated with the images where the measurement was made; and
      retrieving, from the set of electronically formatted images, the electronically formatted images in the extracted references where there is a measurement; and
   virtually displaying the retrieved images with the references and the description.

2. The method of claim 1, wherein at least one of the annotations is not visible in the image.

3. The method of claim 1, further comprising:
   moving information from the visually displayed retrieved images with the references and the description to the visually displayed report in response to receiving a user input.

4. The method of claim 1, further comprising:
   employing a natural language processing module to extract the reference; from the electronically formatted medical report.

5. The method of claim 4, further comprising:
   employing a natural language processing module to extract the identity of tissue from the extracted references.

6. The method of claim 1, further comprising:
   employing a natural language processing module to extract the description.

7. The method of claim 6, further comprising:
   extracting the description from the extracted references.

8. The method of claim 1, further comprising:
   extracting the identity of the tissue from a measurement on the image.

9. The method of claim 1, further comprising:
   extracting the identity of the tissue from an annotation on the image.

10. The method of claim 1, further comprising:
extracting findings and corresponding anatomical positions from the electronically formatted medical report;
labeling the tissue in the images with anatomical labels;
labeling annotations on the image with anatomical labels based on the labeling of the tissue in the image;
matching the findings and the annotations; and
adding a link to the image in the report at the location of the finding, and adding a link to the report in the image at the location of the annotation.

11. The method of claim 10, wherein the link to the image in the report is a hyperlink, and the link to the report in the image is a hyperlink.

12. The method of claim 1, further comprising:
employing a natural language processing module to extract the findings and corresponding anatomical positions from the electronically formatted medical report.

13. The method of claim 1, further comprising:
labeling the tissue in the images using an anatomical atlas or statistical algorithm.

14. A computer readable storage medium encoded with computer readable instructions, which, when executed by a processor, causes the processor to:
visually display an electronically formatted medical report, wherein the electronically formatted medical report references a set of electronically formatted images;
extract the references to the set of electronically formatted images from the electronically formatted medical report;
link the electronically formatted medical report and the set of electronically formatted images by:
determining, from the extracted references, an identity of tissue in each image of the set of electronically formatted images where a measurement was made;
extracting, from the extracted references, a description associated with the images where the measurement was made; and
retrieving, from the set of electronically formatted images, the electronically formatted images in the extracted references where there is a measurement; and
visually display the retrieved images with the references and the description.

15. A computing apparatus, comprising:
a memory with at least one computer readable instruction;
a processor that executes the at least one computer readable instruction, wherein the processor, in response to executing the at least one computer readable instruction,
visually displays an electronically formatted medical report, wherein the electronically formatted medical report references a set of electronically formatted images;
extracts the references to the set of electronically formatted images from the electronically formatted medical report;
links the electronically formatted medical report and the set of electronically formatted images, by:
determining, from the extracted references, an identify of tissue in each image of the set of electronically formatted images where a measurement was made;
extracting, from the extracted references, a description associated with the images where the measurement was made; and
retrieving, from the set of electronically formatted images, the electronically formatted images in the extracted references where there is a measurement; and
visually displays the retrieved images with the references and the description.

* * * * *